(12) United States Patent
Chen et al.

(10) Patent No.: US 12,336,978 B2
(45) Date of Patent: Jun. 24, 2025

(54) PHARMACEUTICAL COMPOSITION CONTAINING AMLODIPINE, CHLORTHALIDONE, AND AMILORIDE AND APPLICATION THEREOF

(71) Applicants: SHENZHEN AUSA PHARMED CO., LTD., Guangdong (CN); SHENZHEN AUSA PHARMACEUTICAL CO., LTD., Guangdong (CN)

(72) Inventors: Guangliang Chen, Guangdong (CN); Duo Yu, Guangdong (CN); Jie Bai, Guangdong (CN); Minqing Tian, Guangdong (CN); Ping Chen, Guangdong (CN); Xiping Xu, Guangdong (CN)

(73) Assignees: SHENZHEN AUSA PHARMED CO., LTD., Shenzhen (CN); SHENZHEN AUSA PHARMACEUTICAL CO., LTD., Shenzhen (CN)

( * ) Notice: Subject to any disclaimer, the term of this patent is extended or adjusted under 35 U.S.C. 154(b) by 896 days.

(21) Appl. No.: 17/489,575

(22) Filed: Sep. 29, 2021

(65) Prior Publication Data
US 2022/0079920 A1    Mar. 17, 2022

Related U.S. Application Data

(63) Continuation of application No. PCT/CN2020/083332, filed on Apr. 3, 2020.

(30) Foreign Application Priority Data

Apr. 8, 2019  (CN) .......................... 201910274749.8

(51) Int. Cl.
| | | |
|---|---|---|
| *A61K 31/4035* | (2006.01) | |
| *A61K 31/4418* | (2006.01) | |
| *A61K 31/4965* | (2006.01) | |

(52) U.S. Cl.
CPC ...... *A61K 31/4035* (2013.01); *A61K 31/4418* (2013.01); *A61K 31/4965* (2013.01)

(58) Field of Classification Search
CPC ........... A61K 31/4035; A61K 31/4418; A61K 31/4965
See application file for complete search history.

(56) References Cited

FOREIGN PATENT DOCUMENTS

| | | | |
|---|---|---|---|
| CN | 1342091 A | 3/2002 | |
| CN | 101730694 A | 6/2010 | |
| CN | 101890166 A | 11/2010 | |
| CN | 101780079 B | 10/2011 | |
| CN | 102145059 B | 6/2012 | |
| CN | 107308181 A | 11/2017 | |
| CN | 110545819 A | 12/2019 | |
| WO | WO-2005070462 A2 * | 8/2005 | ............. A61K 31/41 |
| WO | 2007075542 A2 | 7/2007 | |

OTHER PUBLICATIONS

Sun Ningling et al. "Chinese Expert Consensus on Diagnosis and Treatment of Refractory Hypertension." Chin J of Hypertens 021. 004(2013):321-326.

Daugherty S L , Powers J D , Magid D J , et al. Incidence and prognosis of resistant hypertension in hypertensive patients.[J]. Circulation, 2012, 125(13):1635-1642.

Yu Junke. Analysis of the effect of amlodipine besylate combined with compound amiloride in the treatment of hypertension. Contemporary Medicine Journal 016.018(2018):148-149.

Fuchs, S. C et al. Effectiveness of Chlorthalidone Plus Amiloride for the Prevention of Hypertension: The PREVER-Prevention Randomized Clinical Trial. Journal of the American Heart Association,2016;5:e004248.

* cited by examiner

*Primary Examiner* — Kortney L. Klinkel
*Assistant Examiner* — Richard Grant Peckham

(57) ABSTRACT

Provided herein is a pharmaceutical composition for treating resistant hypertension, which includes amlodipine, chlorthalidone, and amiloride. This disclosure also provides an application of the pharmaceutical composition in the treatment of low renin/low aldosterone resistant hypertension and targeting organ damage in the subject suffering from resistant hypertension.

18 Claims, No Drawings

PHARMACEUTICAL COMPOSITION CONTAINING AMLODIPINE, CHLORTHALIDONE, AND AMILORIDE AND APPLICATION THEREOF

CROSS-REFERENCE TO RELATED APPLICATIONS

This application is a continuation of International Patent Application No. PCT/CN2020/083332, filed on Apr. 3, 2020, which claims the benefit of priority from Chinese Patent Application No. 201910274749.8, filed on Apr. 8, 2019. The content of the aforementioned applications, including any intervening amendments thereto, is incorporated herein by reference in its entirety.

TECHNICAL FIELD

This application relates to pharmaceutical compositions, and more particularly to a pharmaceutical composition for treating resistant hypertension and an application thereof, where the pharmaceutical composition includes amlodipine, chlorthalidone and amiloride.

BACKGROUND

Resistant hypertension (RH) is defined as blood pressure that remains above goal despite use of three sufficient anti-hypertensive medications commonly including a diuretic for at least 1 month or a hypertensive patient who requires 4 or more agents for adequate blood pressure (BP) control. 15-20% of hypertensive patients are resistant hypertension. (Ningling Sun, Yong Huo, Jiguang Wang, et al. Chinese Expert Consensus on Diagnosis and Treatment of Resistant Hypertension [J]. *Chinese Journal of Hypertension*, 2013, 21 (4), 321-326 DOI:CNKI:SUN:ZGGZ.0.2013-04-012). The pathophysiology of RH is multifaceted, and is related to the central and local neurohumoral mechanisms. High salt intake, obesity, and decreased carotid baroreflex are basic factors that lead to the difficulty in controlling blood pressure in those with resistant hypertension. In addition, the renin-angiotensin-aldosterone system (RAAS) activation and the excessive increase of sympathetic nerve activity in central or local tissues, especially the kidney, would initiate inflammatory factors and oxidative stress processes and lead to the progression and occurrence of atherosclerosis, aggravating the abnormalities in vascular structures and functions and making it difficult to control the blood pressure.

Apart from the treatment resistance, the resistant hypertension is more likely to damage the target organ and increase the morbidities of cardiovascular, cerebrovascular and kidney diseases. Daugherty et al. conducted a large-scale clinical trial. Over 3.8 years of follow-up, it was found that 1972 cases (11%) developed chronic kidney disease; 344 patients died; and 234 cases suffered cardiovascular and cerebrovascular diseases (90 cases of non-fatal myocardial infarction, 91 cases of stroke and 53 cases of congestive heart failure) (Daugherty S L, Powers J D, Magid D J, et al. Incidence and prognosis of resistant hypertension in hypertensive patients [J].Circulation, 2012, 125 (13): 1635-1642).

In addition to modifying the lifestyle such as losing weight, restricting the salt intake, reducing the alcohol intake and doing more exercise, the treatment of RH is also performed using a three-drug combinative therapy including a RAAS inhibitor [angiotensin converting enzyme inhibitor (ACEI) or angiotensin receptor blocker (ARB)], a calcium channel blocker and a thiazide diuretic. When the blood pressure still fails to meet the standard, the spironolactone maybe added (renal function and potential risk of hyperkalemia need to be evaluated), a combined β-receptor blocker or an a β-receptor blockers or α-receptor blocker. More seriously, clonidine, reserpine or one of central nervous system inhibitory drugs may be used as the fifth antihypertensive drug to be supplemented to the combination regimen. Unfortunately, there is no "optimal portfolio" for treating the resistant hypertension at present, and a desired drug combination has still not been developed and commercialized.

The drugs containing Chinese medicine ingredients have been disclosed for treating the resistant hypertension. For example, Chinese patent application No. 201710585463.2 discloses a compound preparation which combines *Ganoderma lucidum* polysaccharides with a variety of antihypertensive drugs for RH therapy. Such compound preparation is appreciated by easy administration. Chinese patent application No. 201110086573.7 also provides a traditional Chinese medicine for treating the resistant hypertension, which is composed of sea buckthorn, thyme, *Catharanthus roseus*, *Ganoderma lucidum*, black fungus, *Phyllanthus emblica* root, *Rhodiola*, *Rauwolfia*, *Pueraria*, hawthorn and *cassia* seed. Nevertheless, the mechanism of traditional Chinese medicine (TCM) is complex, and Chinese medicines are usually slow-acting. Such a long treatment period is not suitable for treating the resistant hypertension, and the long-time elevated blood pressure would greatly threaten the health of the patients.

At present, no single drug or fixed-dose combinative drug is approved for treating the resistant hypertension.

Amlodipine is a long-acting dihydropyridine calcium channel blocker (CCB), which blocks the calcium ions outside the vascular smooth muscle cell from entering the cell through the calcium ion channel of the cell membrane, so as to relax the vascular smooth muscle, expand peripheral blood vessels and reduce peripheral resistance. Amlodipine is clinically used to treat high blood pressure and angina pectoris. Compared with the other CCBs, amlodipine has a longer action, less and lighter side effects, and thus becomes the first-line drug for clinical treatment of hypertension.

Chlorthalidone alleviates edema through inhibiting the $Na^+$—$Cl^-$ symporter at the beginning of renal distal convoluted tubules, reducing the reabsorption of $Na^+$, $Cl^-$ and water, and reducing the volume of extracellular fluid through excreting extra sodium and water in the body. The reasons for edema include congestive heart failure, acute emphysema, ascites of liver disease, nephrotic syndrome, acute and chronic nephritis. Chlorthalidone is an auxiliary drug for treating those diseases. As for lowering blood pressure, chlorthalidone is mainly used to treat mild-to-moderate hypertension and heart failure complicated by elderly hypertension.

Amiloride is a potassium-sparing diuretic that acts on the distal renal tubules and collecting ducts. By blocking sodium channel and inhibiting $Na^+$—$H^+$ and $Na^+$—$K^+$ exchange, amiloride can promote the excretion of sodium and chlorine and reduce the secretion of $K^+$ and $H^+$. Due to the weak sodium excretion and BP-lowering activity, amiloride is suitable for the treatment of chronic congestive heart failure, liver cirrhosis with ascites, and hypokalemia caused by primary aldosteronism.

The existing antihypertensive combinations are mainly aimed at hypertension, not the resistant hypertension. The triple combination of three antihypertensive drugs includes amlodipine/valsartan/hydrochlorothiazide tablets and amlodipine/telmisartan/hydrochlorothiazide tablets, which are indicated for primary hypertension but not for the initial treatment of hypertension. There are also some combination drugs being developed. For example, Chinese patent application No. 201010116867.5 discloses a compound pharmaceutical composition containing L-amlodipine for the treatment of hypertension, which comprises L-amlodipine or a pharmaceutically acceptable salt thereof, and chlorthalidone. Yu J reported that amlodipine besylate plus amiloridecan effectively reduce blood pressure of the patients with hypertension (Junke Yu, et al. Analysis of the effect of amlodipine besylate in combination with amilorideon blood pressure lowering [J]. *Contemporary Medicine*, 2018, 18:148-149CNKI:SUN: QYWA.0.2018-18-108). Fuchs Sandra Costa reported that the combination of chlorthalidone with amiloride at low-dose can effectively reduce the risk of BP elevation (Sandra Costa Fuchs, Carlos E. Polide-Figueiredo, José A. FigueiredoNeto, et al. Effectiveness of chlorthalidone plus amiloride for the prevention of hypertension: the PREVER-prevention randomized clinical trial [J]. J Am Heart Assoc. 2016; 5:e004248). Nevertheless, all the above-mentioned prescriptions have no effect on the resistant hypertension. Finding a scientific and innovative therapy for the resistant hypertension is imperative.

SUMMARY

With the development of precision medicine, typing of resistant hypertension should be carried out in which renin and aldosterone may be regarded as biomarkers. According to the plasma concentrations of renin and aldosterone, resistant hypertension can be divided into three subtypes: low-renin/high-aldosteroneresistant hypertension, low-renin/low-aldosteroneresistant hypertension, and high-renin/high-aldosteroneresistant hypertension.

A purpose of the present disclosure is to provide a pharmaceutical composition for treating resistant hypertension, especially for low-renin/low-aldosterone resistant hypertension.

Technical solutions of the present disclosure to achieve the above objective are described as follows.

A pharmaceutical composition for treating resistant hypertension, comprising:
(a) 2.5-10 mg of amlodipine;
(b) 12.5-100 mg of chlorthalidone;
(c) 2.5-20 mg of amiloride; and
(4) a pharmaceutically acceptable carrier.

The pharmaceutical composition disclosed herein is a fixed dose combination.

In some embodiments, the amlodipine is in form of a pharmaceutically acceptable salt, an ester, an active metabolite or a medicinal precursor thereof. The amlodipine provided herein is used as a pharmaceutical component. A medical dose of the amlodipine is 2.5-10 mg; preferably 5 mg-10 mg. The medicinal dose of the amlodipine in form of the salt, the ester, the active metabolite or the medicinal precursor may be converted accordingly.

In some embodiments, the chlortalidone is in form of a pharmaceutically acceptable salt, an ester, an active metabolite or a medicinal precursor thereof. The amlodipine provided herein is used as a pharmaceutical component. A medical dose of the chlorthalidone is 12.5-100 mg; preferably 12.5-50 mg. The medicinal dose of the chlorthiazone in form of the salt, the ester, the active metabolite or the medicinal precursor may be converted accordingly.

In some embodiments, the amiloride is in form of a pharmaceutically acceptable salt, an ester, an active metabolite or a medicinal precursor thereof. The amlodipine provided herein is used as a pharmaceutical component. A medical dose of the amiloride is about 2.5-20 mg; preferably 5-10 mg. The medicinal dose of the amiloride in form of the salt, the ester, the active metabolite or the medicinal precursor may be converted accordingly.

The medicinal dose of the effective component of the composition refers to the dose range in which the effective component is combined with other effective components in the composition to make the composition exert its efficacy. The pharmacodynamic effect of the preferred dose of the composition is better than that of the medicinal dose. Generally, the medicinal dose of the active ingredient of the composition includes the best dose or the best dose range to maximize the efficacy of the composition, which will benefit the patient more.

In some embodiments, the pharmaceutical composition comprises 5 mg of the amlodipine, 12.5 mg of the chlorthalidone and 5 mg of the amiloride.

In some embodiments, the pharmaceutical composition comprises 5 mg of the amlodipine, 12.5 mg of the chlorthalidone and 10 mg of the amiloride.

In some embodiments, the pharmaceutical composition comprises 5 mg of the amlodipine, 25 mg of the chlorthalidone and 5 mg of the amiloride.

In some embodiments, the pharmaceutical composition comprises 5 mg of the amlodipine, 25 mg of the chlorthalidone and 10 mg of the amiloride.

In some embodiments, the pharmaceutical composition comprises 5 mg of the amlodipine, 50 mg of the chlorthalidone and 10 mg of the amiloride.

In some embodiments, the pharmaceutical composition comprises 10 mg of the amlodipine, 12.5 mg of the chlorthalidone and 5 mg of the amiloride.

In some embodiments, the pharmaceutical composition comprises 10 mg of the amlodipine, 12.5 mg of the chlorthalidone and 10 mg of the amiloride.

In some embodiments, the pharmaceutical composition comprises 10 mg of the amlodipine, 25 mg of the chlorthalidone and 5 mg of the amiloride.

In some embodiments, the pharmaceutical composition comprises 10 mg of the amlodipine, 25 mg of the chlorthalidone and 10 mg of the amiloride.

The pharmaceutical composition comprises the pharmaceutically acceptable carrier, and can be made into an ordinary oral preparation such as a tablet, a capsule, a pill and a granule. When being made into the tablet, the pharmaceutical composition is formulated with an excipient and an adjuvant, which are selected from the group consisting of microcrystalline cellulose, an inorganic salt, lactose, sodium chloride, citric acid, sodium sulfite and a combination thereof. Such way is known by those skilled in the art.

The pharmaceutical composition disclosed herein is capable of effectively lowering the blood pressure of a patient with the resistant hypertension, especially the low-renin/low-aldosterone resistant hypertension. Active ingredients of the pharmaceutical composition disclosed herein includes amlodipine, chlorthalidone and amiloride. The three drugs may be used alone or in combination with other antihypertensive drugs in the treatment of hypertension. Amlodipine, chlorothiazone and amiloride are commonly used antihypertensive drugs. As described in the background technology, the above drugs can also be used for the treatment of hypertension alone or in combination with other antihypertensive drugs, but there is no efficacy for the treatment of resistant hypertension at present. In addition, the antihypertensive effect of the pharmaceutical composition provided herein lasts for a long time, and the fluctuation of the blood pressure is small throughout the day. After administration once a day, the blood pressure can be smoothly reduced for 24 hours.

In addition, the pharmaceutical composition provided herein may protect a target organ of the patient with the resistant hypertension, and thus reduce the risk of cardiovascular events. Target organ damage caused by the resistant hypertension includes left ventricular hypertrophy, benign arteriole nephrosclerosis, malignant arteriole nephrosclerosis, renal failure, retinal arteriosclerosis and hypertensive fundus disease. When the damages disclosed herein cannot be effectively controlled, it will lead to cerebrovascular events, including cerebral infarction and cerebral hemorrhage, namely stroke. The pharmaceutical composition disclosed herein can lower blood pressure steadily within 24 hours so that the damage to target organs can be reduced. Furthermore, the resistant hypertension is prone to inducing vascular remodeling, endothelial dysfunction, excessive activation of the sympathetic nerve and renin-angiotensin system, abnormal metabolism and inflammation. The pharmaceutical composition provided herein improves these pathophysiological changes in a synergistical way, effectively protecting the target organs of resistant hypertension.

It should be understood that doses provided herein are not intended to limit the present disclosure, and are merely preferred doses of the present disclosure. Normally, within this range of dose, the pharmaceutical composition is capable of producing an optimal therapeutic effect on individuals with the resistant hypertension.

DETAILED DESCRIPTION OF EMBODIMENTS

The present disclosure will be further described below with reference to the embodiments, and these embodiments are not intended to limit this disclosure. Equivalent replacements made by those skilled in the art without departing from the spirit of the present disclosure should fall within the scope of the present disclosure.

Examples 1-11 Preparation of Tablets (1000 Pieces) Containing Amlodipine, Chlorthalidone and Amiloride

Example 12 Preparation of Capsules (1000 Capsules) Containing Amlodipine, Chlorthalidone and Amiloride Formula composition: 5 g of amlodipine, 12.5 g of chlorthalidone, 5 g of amiloride, 98 g of lactose, 45 g of microcrystalline cellulose, 2 g of carboxymethyl starch sodium, an appropriate amount of 10% povidone K-30 (solvent, absolute ethanol) and 5 g of glyceryl behenate.

Preparation Process

According to the formula composition, lactose, microcrystalline cellulose and carboxymethyl starch sodium were dried at about 100° C. for about 2 hours, respectively. The carboxymethyl starch sodium was sieved using a 100-mesh sieve, and the lactose and the microcrystalline cellulose were sieved using an 80-mesh sieve. After being sieved using a 100-mesh sieve, the medicine was evenly mixed with the above-mentioned auxiliary material mixture followed by granulating. The granulates were mixed with an appropriate amount of glyceryl behenate, and filled into No. 3 capsules to obtain 1000 capsules.

Example 13 Preparation of Capsules (1000 Capsules) Containing Amlodipine, Chlorthalidone and Amiloride Formula composition: 10 g of amlodipine, 25 g of chlorthalidone, 10 g of amiloride, 98 g of lactose, 45 g of microcrystalline cellulose, 2 g of carboxymethyl starch sodium, an appropriate amount of 10% povidone K-30 (solvent, absolute ethanol) and 5 g of glyceryl behenate.

The preparation process adopted herein was basically the same as that used in Example 12.

Example 14 the Effect of Blood Pressure-Lowering and Target Organ Protection of a Combination (Amlodipine/Chlorthalidone/Amiloride) on Deoxycorticosterone-Acetate (DOCA) Salt-Type Hypertensive Rats Methods Animal Model Preparation 94 male Sprague-Dawley (SD) rats, weighting 200-220 g, were fed with ordinary diet. After 7 days of quarantine, the

| Ingredients | Example 1 | Example 2 | Example 3 | Example 4 | Example 5 | Example 6 | Example 7 | Example 8 | Example 9 | Example 10 | Example 11 |
|---|---|---|---|---|---|---|---|---|---|---|---|
| Amlodipine | 2.5 g | 10 g | 5 g | 5 g | 5 g | 5 g | 5 g | 10 g | 10 g | 10 g | 10 g |
| Chlorthalidone | 12.5 g | 100 g | 12.5 g | 12.5 g | 25 g | 25 g | 50 g | 12.5 g | 12.5 g | 25 g | 25 g |
| Amiloride | 2.5 g | 20 g | 5 g | 10 g | 5 g | 10 g | 10 g | 5 g | 10 g | 5 g | 10 g |
| Pregelatinized Starch | 22 g | 60 g | 45 g | 45 g | 81 g | 79 g | 62 g | 76 g | 90 g | 87 g | 88 g |
| Microcrystalline cellulose | 76 g | 112 g | 160 g | 160 g | 122 g | 118 g | 92 g | 113 g | 134 g | 130 g | 133 g |
| Carboxymethyl starch sodium | 3 g | 7.5 g | 5 g | 5 g | 6 g | 6.4 g | 4 g | 5 g | 6 g | 6.4 g | 7 g |
| Sodium dodecyl sulfate | 0.45 g | 3.6 g | 0.9 g | 0.9 g | 1.8 g | 1.8 g | 0.45 g | 0.9 g | 0.9 g | 1.8 g | 1.8 g |
| 10% povidone K-30 | right amount | right amount | right amount | right amount | right amount | right amount | right amount | right amount | right amount | right amount | right amount |
| Magnesium stearate | 0.75 g | 2.5 g | 1.5 g | 1.5 g | 1.5 g | 1.5 g | 1.5 g | 1.5 g | 1.5 g | 1.5 g | 1.5 g |

Preparation Process

Amlodipine, chlorthalidone and amiloride were mixed, and added with starch sodium, sodium lauryl sulfate followed by mixing. Microcrystalline cellulose and pregelatinized starch were then added and evenly mixed to obtain a mixture. The mixture was made into a soft material using an appropriate amount of a 10% povidone K-30 alcohol solution, and then was subjected to granulating, drying, and granulating to obtain granules. The granules with a water content of about 3% were evenly mixed with an appropriate amount of magnesium stearate, and then compressed into 1000 tablets.

basal blood pressure was measured. 10 rats were randomly selected as a sham group and fed with ordinary diet until the end of the experiment. The remaining 84 rats were used as a model group, and deoxycorticosterone-acetate (DOCA) silicone tubes (100 mg/rat) were implanted subcutaneously. The rats in the model group were anesthetized by intraperitoneal injection of 0.8% pentobarbital sodium, and fixed in the back position followed by routine disinfection. The abdominal cavity of those rats was opened to find the left kidney, and then the renal artery and vein were ligated to remove the left kidney. The abdominal cavity was sprinkled with 0.2 mL of penicillin, and then sutured layer by layer. 100000 units of penicillin sodium were injected intraperitoneally once a day for 2 consecutive days. The DOCA silicone tube was embedded subcutaneously in the right abdomen followed by suturing (GE Shunna et al., Establishment of DOCA salt-type hypertensive rat model [J] *Chinese Pharmacology Bulletin,* 2010; 26 (6): 832-835). Routine rearing was carried out after the operation, and those rats were also fed with 1% saline at the same time. The rats in the sham group experienced the same operations of the anaesthesia, abdominal cavity incision and left kidney determination, but no ligation and removal of the left kidney were performed. The right side of the abdomen was embedded with powder-free silicone tube, and penicillin anti infection injection was also performed 2 days later, with normal drinking water. The blood pressure of rats was measured in the second and fourth weeks of modeling (taking the average value of 3 consecutive times after the measurement was stable) to verify the success of the modeling.

Randomization and Dosing Procedure

The blood pressure was measured 4 weeks after modeling, and the model was successful if the blood pressure was stable above 140 mmHg. The 70 rats that were successfully modeled were randomly divided into a model group and administration groups according to their blood pressures, with 10 rats in each group. The administration volume was 1 mL/100 g body weight, once a day, for 13 consecutive weeks. The control drug was amlodipine/valsartan/hydrochlorothiazide tablets, the dual drug was a combination of raw materials, and the test drug was the compound prepared in the Examples 5 and 11, which was converted into the required dose of rats according to the body surface area.

Detection Data Collection (1) After the modeling, the levels serum renin and aldosterone in the rats before the administration and after the grouping were measured. (2) Blood pressure was measured before the administration and after 4-week administration, 8-week administration and 13-week administration. (3) Indicators of the renal function included proteinuria, microalbuminuria, creatinine clearance and blood urea nitrogen. (4) Indicators of the heart function included left ventricular index, heart index and brain natriuretic peptide level.

Results (1) Serum Aldosterone (ALD) and Renin (REN) Levels in Model Rats

The levels of ALD and REN in the rats of the model group were lower than those in the rats of the sham group ($P<0.01$) (shown in Table 1).

TABLE 1

Levels of ALD and REN in the rats of each group before administration ($\bar{x} \pm s$, n = 10)

| Group | Dose (mg/kg) | ALD (pg/mL) | REN (pg/mL) |
| --- | --- | --- | --- |
| Sham group | — | 189.27 ± 34.25 | 190.83 ± 27.08 |
| Model group | — | 118.49 ± 20.52## | 129.54 ± 25.74## |
| Amlodipine/ valsartan/ hydrochlorothiazide tablet | 1 + 16 + 2.5 | 127.54 ± 26.64## | 132.18 ± 21.98## |
| Amlodipine/ chlortalidone/ amiloride | 0.5 + 2.5 + 0.5 | 108.00 ± 27.34## | 127.54 ± 22.11## |
| Amlodipine/ chlortalidone/ amiloride | 1 + 2.5 + 1 | 119.06 ± 21.26## | 129.08 ± 29.78## |

TABLE 1-continued

Levels of ALD and REN in the rats of each group before administration ($\bar{x} \pm s$, n = 10)

| Group | Dose (mg/kg) | ALD (pg/mL) | REN (pg/mL) |
| --- | --- | --- | --- |
| Amlodipine + chlortalidone | 1 + 2.5 | 112.79 ± 28.94## | 131.09 ± 20.77## |
| Amlodipine + amiloride | 1 + 1 | 124.17 ± 30.66## | 136.35 ± 28.06## |
| Chlortalidone + amiloride | 2.5 + 1 | 118.99 ± 22.08## | 128.55 ± 25.00## |

Compared with the sham group, #P < 0.05, ##P < 0.01.

(2) Effect of the Combination (Amlodipine/Chlorthalidone/Amiloride) on the Blood Pressure of Rats In administration period, compared with the sham group, the blood pressure of the rats in the model group increased significantly. Compared with the model group, the blood pressure of the rats in the amlodipine/valsartan/hydrochlorothiazide tablet group, groups with different dose of amlodipine/chlorthalidone/amiloride tablet, the amlodipine+chlorthalidone group, the amlodipine+amiloride group and the chlorthalidone+amiloride group decreased, and there was statistical difference compared with the model group. Compared with the control drug amlodipine/valsartan/hydrochlorothiazide tablet group, blood pressure of the rats in the low-dose amlodipine/chlorthalidone/amiloride tablet group can be further reduced by 6.8-11.4 mmHg, and the antihypertensive effect of the high-dose group was significantly enhanced ($P<0.05$). Compared with the two-component drug, the three-component drug group can lower blood pressure better, and the further blood pressure-lowering can reach 10.9-24.2 mmHg (shown in Tables 2-1 and 2-2).

TABLE 2-1

Effects of amlodipine/chlorhexidine/amiloride compound preparation on blood pressure of rats ($\bar{x} \pm s$, n = 8-10)

| Group | Dose (mg/kg) | SBP (mmHg) Before administration | SBP (mmHg) Administration for 4 weeks |
| --- | --- | --- | --- |
| Sham group | | 119.24 ± 21.3 | 120.7 ± 15.6 |
| Model group | | 175.38 ± 19.8## | 172.3 ± 20.8## |
| Amlodipine/ valsartan/ hydrochlorothiazide tablet | 1 + 16 + 2.5 | 174.65 ± 18.9 | 161.4 ± 25.2 |
| Amlodipine/ chlortalidone/ amiloride | 0.5 + 2.5 + 0.5 | 175.47 ± 22.7 | 144.6 ± 18.5*■▲ |
| Amlodipine/ chlortalidone/ amiloride | 1 + 2.5 + 1 | 176.53 ± 21.6 | 133.9 ± 21.5**■■▲★ |
| Amlodipine + chlortalidone | 1 + 2.5 | 172.89 ± 25.8 | 150.0 ± 16.4* |
| Amlodipine + amiloride | 1 + 1 | 176.32 ± 24.4 | 154.8 ± 17.6* |
| Chlortalidone + amiloride | 2.5 + 1 | 175.93 ± 27.5 | 153.5 ± 24.7* |

Compared with the sham group, #P < 0.05, ##P < 0.01; compared with the model group, *P < 0.05, **P < 0.01; compared with the amlodipine/valsartan/hydrochlorothiazide tablet group, ■P < 0.05, ■■P < 0.01; compared with the amlodipine + chlorthalidone group, ▲P < 0.05, ▲▲P < 0.01; compared with the amlodipine + amiloride group, ▲P < 0.05, ▲▲P < 0.01; and compared with the chlorthalidone + amiloride group, ★P < 0.05, ★★P < 0.01.

TABLE 2-2

Effects of amlodipine/chlorhexidine/amiloride compound preparation on blood pressure of rats ($\bar{x} \pm s$, n = 8-10)

| Group | Dose (mg/kg) | SBP (mmHg) Administration for 8 weeks | Administration for 13 weeks |
|---|---|---|---|
| Sham group | — | 112.6 ± 14.3 | 115.5 ± 21.1 |
| Model group | — | 178.3 ± 22.8## | 183.9 ± 23.9## |
| Amlodipine/valsartan/hydrochlorothiazide tablet | 1 + 16 + 2.5 | 154.6 ± 20.3* | 151.3 ± 16.4* |
| Amlodipine/chlortalidone/amiloride | 0.5 + 2.5 + 0.5 | 139.3 ± 19.8**■★ | 131.7 ± 18.6**■△ |
| Amlodipine/chlortalidone/amiloride | 1 + 2.5 + 1 | 128.5 ± 21.7**■△▲★★ | 122.2 ± 15.4**■△★ |
| Amlodipine + chlortalidone | 1 + 2.5 | 145.4 ± 22.1* | 146.9 ± 14.2* |
| Amlodipine + amiloride | 1 + 1 | 146.3 ± 20.4* | 142.3 ± 18.8** |
| Chlortalidone + amiloride | 2.5 + 1 | 152.7 ± 21.5* | 149.8 ± 19.8* |

Compared with the sham group, #P < 0.05, ##P < 0.01; compared with the model group, *P < 0.05, **P < 0.01; compared with the amlodipine/valsartan/hydrochlorothiazide tablet group, ■P < 0.05, ■■P < 0.01; compared with the amlodipine + chlorthalidone group, △P < 0.05, △△P < 0.01; compared with the amlodipine + amiloride group, ▲P < 0.05, ▲▲P < 0.01; and compared with the chlorthalidone + amiloride group, ★P < 0.05, ★★P < 0.01.

(3) Effect of Amlodipine/Chlorthalidone/Amiloride Compound Preparation on Renal Function of Rats After 13-week administration, 24-hour urine of the rats was collected for urinary protein and urinary microalbumin (MALB) detection. The 24-hour urine protein and MALB in the rats of the model group were significantly higher than those in the rats of the sham group. Compared with the model group, the 24-hour urine protein and MALB in the rats of the amlodipine/chlortalidone/amiloride tablet group decreased (P<0.01). Compared with the amlodipine/valsartan/hydrochlorothiazide tablet group and each dual drug combination, the compound preparation had significantly enhanced the effect in improving renal function in this model animal.

The creatinine clearance rate of the model group decreased, and the urea nitrogen level increased significantly, which was significantly different from the sham group. The creatinine clearance rate of the amlodipine/chlorthalidone/amiloride tablet group increased, and the urea nitrogen decreased, which were better than those of the amlodipine/valsartan/hydrochlorothiazide tablet group (P<0.05, P<0.01). Compared with the dual drug combination, the compound preparation can further improve renal function, indicating that the compound preparation administration group had a significant protective effect on the kidney (shown in Tables 3-1 and 3-2).

TABLE 3-1

Effects of amlodipine/chlorthalidone/amiloride compound preparation on renal function of rats ($\bar{x} \pm s$, n = 8-10)

| Group | Dose (mg/kg) | Urine protein (mg) | MALB (mg) |
|---|---|---|---|
| Sham group | — | 1.9 ± 0.6 | 202.7 ± 87.2 |
| Model group | — | 6.0 ± 2.6## | 685.4 ± 204.4## |
| Amlodipine/valsartan/hydrochlorothiazide tablet | 1 + 16 + 2.5 | 5.1 ± 1.2* | 585.8 ± 141.0* |
| Amlodipine/chlortalidone/amiloride | 0.5 + 2.5 + 0.5 | 3.8 ± 1.3**■▲ | 389.8 ± 105.0**■▲★ |
| Amlodipine/chlortalidone/amiloride | 1 + 2.5 + 1 | 3.1 ± 1.1**■■▲▲★ | 363.3 ± 87.7**■■▲▲★★ |
| Amlodipine + chlortalidone | 1 + 2.5 | 4.0 ± 1.2** | 589.6 ± 124.2** |
| Amlodipine + amiloride | 1 + 1 | 5.2 ± 1.6* | 516.3 ± 112.8** |
| Chlortalidone + amiloride | 2.5 + 1 | 4.3 ± 1.8** | 595.4 ± 79.6** |

Compared with the sham group, #P < 0.05, ##P < 0.01; compared with the model group, *P < 0.05, **P < 0.01; compared with the amlodipine/valsartan/hydrochlorothiazide tablet group, ■P < 0.05, ■■P < 0.01; compared with the amlodipine + chlorthalidone group, △P < 0.05, △△P < 0.01; compared with the amlodipine + amiloride group, ▲P < 0.05, ▲▲P < 0.01; and compared with the chlorthalidone + amiloride group, ★P < 0.05, ★★P < 0.01.

TABLE 3-2

Effects of amlodipine/chlorthalidone/amiloride compound preparation on renal function of rats ($\bar{x} \pm s$, n = 8-10)

| Group | Dose (mg/kg) | Creatinine clearance (mL/min) | Blood urea nitrogen (mmol/L) |
|---|---|---|---|
| Sham group | — | 1.42 ± 0.29 | 7.24 ± 1.59 |
| Model group | — | 0.59 ± 0.12## | 16.35 ± 2.76## |
| Amlodipine/valsartan/hydrochlorothiazide tablet | 1 + 16 + 2.5 | 0.72 ± 0.15* | 14.07 ± 3.12* |
| Amlodipine/chlortalidone/amiloride tablet | 0.5 + 2.5 + 0.5 | 0.85 ± 0.22**▲ | 12.26 ± 3.55**▲ |
| | 1 + 2.5 + 1 | 0.93 ± 0.23**■△▲★ | 10.33 ± 2.87**■△▲★ |
| Amlodipine + chlortalidone | 1 + 2.5 | 0.75 ± 0.17** | 13.56 ± 2.96* |
| Amlodipine + amiloride | 1 + 1 | 0.71 ± 0.16* | 14.27 ± 3.13 |
| Chlortalidone + amiloride | 2.5 + 1 | 0.72 ± 0.21* | 14.19 ± 3.06* |

Compared with the sham group, #P < 0.05, ##P < 0.01; compared with the model group, *P < 0.05, **P < 0.01; compared with the amlodipine/valsartan/hydrochlorothiazide tablet group, ■P < 0.05, ■■P < 0.01; compared with the amlodipine + chlorthalidone group, △P < 0.05, △△P < 0.01; compared with the amlodipine + amiloride group, ▲P < 0.05, ▲▲P < 0.01; and compared with the chlorthalidone + amiloride group, ★P < 0.05, ★★P < 0.01.

(4) Protective Effect of Amlodipine/Chlorthalidone/Amiloride Compound Preparation on Rat Heart Brain natriuretic peptide (BNP) gene is an acute cardiac response gene, which can stimulate the synthesis and release of brain natriuretic peptide when myocardial ischemia and ventricular wall stress increase. After 13-week administration, the rats were sacrificed and blood was collected to detect plasma brain natriuretic peptide levels. The hearts were weighed, and the left ventricles were separated and weighed to calculate the left ventricular index ((left ventricle weight/heart weight*1000)/body weight of each group of rats). Compared with the sham group, the left ventricular index of the rats in the model group was significantly increased, indicating the presence of left ventricular hypertrophy. Compared with the sham group, the left ventricular index of the rats in the model group was significantly increased, indicating the presence of left ventricular hypertrophy. Amlodipine/valsartan/hydrochlorothiazide tablets have a certain improving effect, but the effect is not as good as the amlodipine/chlorthalidone/amiloride tablet group (P<0.05). The BNP of the rats in the model group was significantly increased, suggesting that there is an acute cardiac reaction. The BNP of the rats in the amlodipine/chlorthalidone/amiloride tablet group was significantly reduced (P<0.01), and compared with the dual drug combination, the cardio protective effect was more obvious (shown in Table 4).

TABLE 4

Effects of amlodipine/chlorthalidone/amiloride compound preparation on cardiac function of rats ($\bar{x} \pm s$, n = 8-10)

| Group | Dose (mg/kg) | Left ventricular mass index (mg/g) | BNP (ng/L) |
|---|---|---|---|
| Sham group | — | 1.34 ± 0.15 | 28.45 ± 3.05 |
| Model group | — | 2.42 ± 0.24## | 58.97 ± 4.21## |
| Amlodipine/ valsartan/ hydrochloro- thiazide tablet | 1 + 16 + 2.5 | 1.61 ± 0.21 | 47.04 ± 3.89* |
| Amlodipine/ chlortalidone/ amiloride tablet | 0.5 + 2.5 + 0.5 | 1.55 ± 0.17** | 39.21 ± 4.95**■△★ |
| | 1 + 2.5 + 1 | 1.43 ± 0.33**■△▲★ | 33.43 ± 4.13**■■△△▲▲★★ |
| Amlodipine + chlortalidone | 1 + 2.5 | 1.67 ± 0.26* | 47.23 ± 3.76 |
| Amlodipine + amiloride | 1 + 1 | 1.63 ± 0.22 | 45.59 ± 3.28* |
| Chlortalidone + amiloride | 2.5 + 1 | 1.68 ± 0.24* | 51.46 ± 4.09 |

Compared with the sham group, #P < 0.05, ##P < 0.01; compared with the model group, *P < 0.05, **P < 0.01; compared with the amlodipine/valsartan/hydrochlorothiazide tablet group, ■P < 0.05, ■■P < 0.01; compared with the amlodipine + chlorthalidone group, △P < 0.05, △△P < 0.01; compared with the amlodipine + amiloride group, ▲P < 0.05, ▲▲P < 0.01; and compared with the chlorthalidone + amiloride group, ★P < 0.05, ★★P < 0.01.

(5) Stroke During the Experiment

The No. 4 rat in the model group developed unstable standing and tilted head to one side after 8-week administration, and died after one-week independent observation. The blood pressure of the No.4 rat was 191 mmHg after 8-week administration. The No. 2 rat in the model group showed hemiplegia, unstable standing and rotating gait, and tilted head to one side after 11-week administration, and died within the 11th week. The blood pressure of the No. 2 rat was 205 mmHg after 8-week administration. The No. 5 rat in the amlodipine/valsartan/hydrochlorothiazide tablet group died after 8-week administration, and it were found to have symptoms such as diarrhea and unsteady standing. The blood pressure of the No. 5 rat was 213 mmHg after 4 weeks of administration. The No. 1 rat in the chlorthalidone+amiloride group developed hemiplegia and unstable standing after 3-week administration. According to the symptoms before death, it was initially considered to be a stroke death. No rat in the other groups died.

Example 15 Synergistic Effect of Amlodipine/Chlorthalidone/Amiloride on Blood Pressure-Lowering of DOCA Salt-Type Hypertensive Rats The model preparation method and dosing conversion used herein was basically the same as than adopted in Example 14. Table 5 showed the rat groups, and there were ten rats in each group. Those rats were given intragastric administration once a day for 4 consecutive weeks. The systolic blood pressure of the rats was measured 2 to 4 hours after the last administration. The JinzhengJun Q value method is also called probability addition method. Particularly, according to the pharmacological effects of the combination of the two drugs and the two single drugs, a value of Q is calculated using the formula $Q=E_{A+B}/(E_A+E_B-E_A \times E_B)$, in which, the numerator represents the "measured merger effect"; the denominator represents the "expected merger effect"; and Q is a ratio of the "measured merger effect" to the "expected merger effect". When the Q value is less than 0.85, the combination of the two drugs is considered to be an antagonistic effect; when the Q value is between 0.85 and 1.15, it is considered as an additive effect; and when the Q value is greater than 1.15, it is considered as a synergistic effect. In order to satisfy the analysis of the relationship between the pharmacological effects, the blood pressure value is converted into an effect that can directly reflect the strength of the pharmacological action according to the formula $Ei=(1-P_i/P_{model\ group}) \times 100\%$, where $P_i$ is a blood pressure value of each group; and $P_{model\ group}$ is a blood pressure value of the model group. The results are shown in Table 5.

Results

Compared with the three dual+single-drug combinations, the Q values of the amlodipine/chlorthalidone/amiloride combination group on the systolic blood pressure of DOCA salt hypertensive rats were 1.257, 1.203 and 1.295, which were all lager than 1.15. It showed that the three drugs of the pharmaceutical composition provided herein had a synergistic effect with each other, and the compatibility of the three drugs was reasonable, which can enhance the antihypertensive effect of the drugs on DOCA salt-type hypertensive rats.

Compared with the three dual+single-drug combinations, the Q values of the amlodipine/hydrochlorothiazide/amiloride combination group on systolic blood pressure of DOCA salt-type hypertensive rats were 1.022, 0.920 and 0.986, 0.85<Q<1.15, indicating that the drug composition of amlodipine/hydrochlorothiazide/amiloride had an additive effect on each other. The Q values of the amlodipine/hydrochlorothiazide/spironolactone combination group on the systolic blood pressure of DOCA salt-type hypertensive rats were 0.956, 0.890 and 0.901, 0.85<Q<1.15, indicating that the amlodipine/hydrochlorothiazide/spironolactone composition had an additive effect on each other. The Q values of the amlodipine/valsartan/hydrochlorothiazide combination group on the systolic blood pressure of DOCA salt hypertensive rats were 0.939, 1.010 and 0.975, 0.85<Q<1.15, indicating that the amlodipine/valsartan/hydrochlorothiazide composition had an additive effecton each other.

Compared with the two dual+single-drug combinations, the Q values of the amlodipine/chlorthalidone/spironolactone combination group on the systolic blood pressure of DOCA-type salt hypertensive rats were 0.977 and 0.972, 0.85<Q<1.15, indicating the amlodipine/chlorthalidone/spironolactone composition had an additive effecton each other. The Q values of the amlodipine/valsartan/chlorthalidone combination group on the systolic blood pressure of DOCA salt hypertensive rats were 0.998 and 1.022, 0.85<Q<1.15, indicating that amlodipine/valsartan/chloride composition had an additive effect on each other.

TABLE 5

Synergistic effect of amlodipine/chlorthalidone/amiloride on blood pressure reduction of DOCA salt-type hypertensive rats ($\bar{x} \pm s$, n = 10)

| NO | Group | Dose (mg/kg) | SBP (mmHg) | Conversion value $(1 - P_t/P_{modelgroup}) \times 100\%$ | Q value 1 (First component + second component: third component) | Q value 2 (First component + third component: second component) | Q value 3 (Second component + third component: first component) |
|----|-------|--------------|------------|---------|---------|---------|---------|
| 1 | Sham group | — | 105.3 ± 10.2 | — | | | |
| 2 | Model group | — | 172.2 ± 21.3 | — | | | |
| 3 | Amlodipine (A) | 0.5 | 156.4 ± 19.1 | 0.092 | | | |
| 4 | Chlorthalidone (B) | 1.25 | 160.6 ± 15.5 | 0.067 | | | |
| 5 | Amiloride (C) | 0.5 | 164.5 ± 20.1 | 0.045 | | | |
| 6 | Hydrochlorothiazide (D) | 1.25 | 162.4 ± 16.6 | 0.057 | | | |
| 7 | Valsartan (E) | 8.0 | 158.6 ± 12.2 | 0.079 | | | |
| 8 | Spironolactone (F) | 2.5 | 168.4 ± 13.9 | 0.022 | | | |
| 9 | A + B/amlodipine + chlorthalidone | 0.5 + 1.25 | 145.2 ± 17.9 | 0.157 | | | |
| 10 | A + C/amlodipine + amiloride | 0.5 + 0.5 | 147.1 ± 15.6 | 0.146 | | | |
| 11 | B + C/chlorthalidone + amiloride | 1.25 + 0.5 | 153.8 ± 13.9 | 0.107 | | | |
| 12 | A + D/amlodipin + hydrochlorothiazide | 0.5 + 1.25 | 148.7 ± 14.8 | 0.136 | | | |
| 13 | D + C/hydrochlorothiazide + amiloride | 1.25 + 0.5 | 155.2 ± 18.8 | 0.099 | | | |
| 14 | A + F/amlodipine + spironolactone | 0.5 + 2.5 | 152.1 ± 20.1 | 0.117 | | | |
| 15 | D + F/hydrochlorothiazide + spironolactone | 1.25 + 2.5 | 158.3 ± 19.2 | 0.081 | | | |
| 16 | A + E/amlodipine + valsartan | 0.5 + 8.0 | 142.4 ± 14.8 | 0.173 | | | |
| 17 | E + D/valsartan + hydrochlorothiazide | 8.0 + 1.25 | 149.4 ± 16.4 | 0.132 | | | |
| 18 | A + B + C | 0.5 + 1.25 + 0.5 | 130.1 ± 13.5 | 0.244 | 1.257 | 1.203 | 1.295 |
| 19 | A + D + C | 0.5 + 1.25 + 0.5 | 141.4 ± 13.9 | 0.179 | 1.022 | 0.920 | 0.986 |
| 20 | A + B + F | 0.5 + 1.25 + 2.5 | 142.7 ± 12.2 | 0.171 | 0.977 | 0.972 | — |
| 21 | A + D + F | 0.5 + 1.25 + 2.5 | 146.6 ± 14.8 | 0.149 | 0.956 | 0.890 | 0.901 |
| 22 | A + E + D | 0.5 + 8.0 + 1.25 | 136.6 ± 11.8 | 0.207 | 0.939 | 1.010 | 0.975 |
| 23 | A + E + B | 0.5 + 8.0 + 1.25 | 132.9 ± 16.2 | 0.228 | 0.998 | 1.022 | — |

Example 16 Clinical Trial of Antihypertensive Efficacy and Safety of Amlodipine/Chlorothiazone/Amiloride in Patients with Resistant Hypertension Methods
Inclusion Criteria Subjects should meet all the following criteria, and do not belong to any one of the exclusion criteria.

Patients aged 40 to 75 years; continuously taking 3 or more antihypertensive drugs (one of which is a diuretic) for more than one month, and the sitting blood pressure (average of 3 measurements) meets the following criteria: diastolic blood pressure ≥90 mmHg or systolic blood pressure ≥140 mmHg, and diastolic blood pressure <110 mmHg or systolic blood pressure <180 mmHg; and volunteer to participate and sign an informed consent form.

Exclusion Criteria (1) Pregnant or lactating women; (2) those who have a history of allergy to the ingredients in the drug; (3) those with definite allergic constitution; (4) patients with white coat hypertension; (5) patients with poor medication compliance; (6) patients with known serious medical diseases; (7) those with obvious laboratory examinations or abnormal signs, which may indicate that the patient has a serious disease or may affect the observation and evaluation of the drug efficacy or adverse events according to the judgment of the investigator; and (8) those who have participated in any trial drug that has not been officially approved for marketing within 4 weeks before the first visit.

Randomization and Data Collection

The subjects were randomly divided into groups and intervened in parallel control. The blood pressure of the patients was measured on the 4th weekend and the 8th weekend, respectively. Patients with both systolic and diastolic blood pressure reaching the standard (<140/90 mmHg) were regarded as reaching the standard, and the rate of reaching the standard was calculated. Safety indicators include blood and urine routine, electrocardiogram, liver and kidney function, and adverse events.

Dosing Procedures

Group A

The original treatment plan was continued.

Group B

The original drug was switched to amlodipine/valsartan/hydrochlorothiazide tablets (10/160/25 mg).

Group C

The original drug was switched to a combination of 5-10 mg of amlodipine, 12.5-50 mg of chlorthalidone and 5-10 mg of amiloride.

Results

The blood pressure of most patients in group A could not reach the standard, and the rate of reaching the standard in group B patients increased. The difference was significant in the 4th week. Compared with group A, the blood pressure compliance rate of patients in the amlodipine+chlorthalidone+amiloride treatment group (group C) was significantly increased. The difference between the 4th week and the 8th week was significant. Compared with group B, the blood pressure compliance rate of patients in the amlodipine+chlorthalidone+amiloride treatment group (group C) further improved, and the difference was significant at the 8th week. The results were shown in table 6.

Common adverse events (incidence rate>1%): upper respiratory tract symptoms, pain, abnormal liver function, gastrointestinal symptoms, abnormal lipid metabolism, dizziness, skin itching, urinary system symptoms, cardiovascular symptoms, oral symptoms, abnormal glucose metabolism, and facial flushing. The total incidence of adverse events in each group: group A, 22.0%; group B, 19.8%; and group C, 15.6%. The group C had the lowest incidence of adverse events.

TABLE 6

Effect of amlodipine + chlorthalidone + amiloride on the rate of blood pressure compliance in RH patients

| Group | Drug | Blood pressure compliance rate (%) 4 W | Blood pressure compliance rate (%) 8 W | Adverse event rate (%) |
|---|---|---|---|---|
| Group A | The original treatment plan | 4.7 (4/86) | 6.1 (5/82) | 22.0 (20/91) |
| Group B | Amlodipine/ Valsartan/ Hydrochlorothiazide Tablets | 14.4 (13/90)* | 12.5 (12/96) | 19.8 (19/96) |
| Group C | Amlodipine + chlorthalidone + amiloride | 32.6 (30/92)** | 36.5 (35/96)**# | 15.6 (15/96) |

Compared with the group A: *P < 0.05, **P < 0.01; and compared with group B: #P < 0.05.

Example 17 Clinical Trial of Antihypertensive Efficacy and Safety of Amlodipine/Chlorothiazone/Amiloride in Patients with Low Renin/Low Aldosteroneresistant Hypertension Methods Inclusion Criteria Subjects should meet all the following criteria, and do not involve any one of the exclusion criteria.

Patients aged 40 to 75 years; insist on using 3 or more antihypertensive drugs (one of which is a diuretic) for more than one month; sitting blood pressure (average of 3 measurements) meets the following criteria: diastolic blood pressure ≥90 mmHg or systolic blood pressure ≥140 mmHg, and diastolic blood pressure <110 mmHg or systolic blood pressure <180 mmHg; patients with low renin/low aldosterone measured by fasting blood in the morning; and voluntarily participate and sign an informed consent form.

Exclusion Criteria (1) Pregnant or lactating women; (2) those who have a history of allergies to the ingredients in the medicine; (3) those with clear allergies; (4) patients with white coat hypertension; (5) those with poor medication compliance; (6) patients with known serious medical diseases; (7) those with obvious laboratory examinations or abnormal signs, which may indicate that the patient has a serious disease or may affect the observation and evaluation of the drug efficacy or adverse events according to the judgment of the investigator; (8) those who have participated in any trial drug that has not been officially approved for marketing by the state within 4 weeks before the first visit; (9) patients with high renin or normal renin level determined through taking blood with an empty stomach in the morning; and (10) patients with normal or elevated levels of plasma aldosterone determined through taking blood in the morning with an empty stomach.

Randomization and Data Collection

The subjects were randomly divided into groups and intervened in parallel control. The blood pressure of the patient was measured at the 4th weekend and the 8th weekend, respectively. Patients with both systolic and diastolic blood pressure reaching the standard (<140/90 mmHg) were regarded as reaching the blood pressure standard. Safety indicators include blood and urine routine, electrocardiogram, liver and kidney function, and adverse events.

Dosing Procedures

Group A

The original treatment plan was continued.

Group B

The original drug was switched to amlodipine/valsartan/hydrochlorothiazide tablets (10/160/25 mg).

Group C

The original drug was switched to 5-10 mg of amlodipine+12.5-50 mg of chlorthalidone+5-10 mg of amiloride.

Results

The blood pressure of most patients in group A failed to reach the standard, and the rate of reaching the standard in group B patients increased. The difference between the 4th week and the 8th week was significant. Compared with group A, the blood pressure compliance rate of patients in the amlodipine+chlorthalidone+amiloride treatment group (group C) was significantly increased, and the difference between the 4th and 8th weeks was significant. Compared with group B, the blood pressure compliance rate of patients in the amlodipine+chlorthalidone+amiloride treatment group (group C) further improved, and the difference between the 4th week and the 8th week was significant. The results were shown in Table 7.

Common adverse events (incidence rate>1%): upper respiratory tract symptoms, abnormal liver function, gastrointestinal symptoms, abnormal lipid metabolism, dizziness, skin itching, urinary system symptoms, cardiovascular symptoms, abnormal glucose metabolism, and facial flushing. The total incidence of adverse events in each group: group A, 25.6%; group B, 28.9%; and group C, 18.9%. The group C had the lowest incidence of adverse events.

TABLE 7

Effect of amlodipine + chlorthalidone + amiloride treatment on the compliance rate of blood pressure inpatients with low renin/low aldosterone resistant hypertension

| Group | Drug | Blood pressure compliance rate (%) 4 W | Blood pressure compliance rate (%) 8 W | Adverse event rate (%) |
|---|---|---|---|---|
| Group A | The original treatment plan | 7.5 (6/80) | 6.1 (5/82) | 25.6 (22/86) |
| Group B | Amlodipine/ valsartan/ hydrochloro- thiazide Tablets | 18.1 (15/83)* | 17.4 (15/86)* | 28.9 (36/90) |
| Group C | Amlodipine + chlorthalidone + amiloride | 48.8 (42/86)** | 53.4 (47/88)**,### | 18.9 (17/9) |

Compared with the group A: *P < 0.05, **P < 0.01; and compared with group B: #P < 0.05.

What is claimed is:

1. A pharmaceutical composition for treating resistant hypertension, consisting of:
   (a) 2.5-10 mg of amlodipine;
   (b) 12.5-100 mg of chlorthalidone;
   (c) 2.5-20 mg of amiloride; and
   (d) a pharmaceutically acceptable carrier.

2. The pharmaceutical composition of claim 1, comprising:
   5-10 mg of the amlodipine.

3. The pharmaceutical composition of claim 1, comprising:
   12.5-50 mg of the chlorthalidone.

4. The pharmaceutical composition of claim 1, comprising:
   5-10 mg of the amiloride.

5. The pharmaceutical composition of claim 1, comprising:
   5 mg of the amlodipine;
   12.5 mg of the chlorthalidone; and
   5 mg of the amiloride.

6. The pharmaceutical composition of claim 1, comprising
   5 mg of the amlodipine;
   12.5 mg of the chlorthalidone; and
   10 mg of the amiloride.

7. The pharmaceutical composition of claim 1, comprising:
   5 mg of the amlodipine;
   25 mg of the chlorthalidone; and
   5 mg of the amiloride.

8. The pharmaceutical composition of claim 1, comprising:
   5 mg of the amlodipine;
   25 mg of the chlorthalidone; and
   10 mg of the amiloride.

9. The pharmaceutical composition of claim 1, comprising:
   5 mg of the amlodipine;
   50 mg of the chlorthalidone; and
   10 mg of the amiloride.

10. The pharmaceutical composition of claim 1, comprising:
    10 mg of the amlodipine;
    12.5 mg of the chlorthalidone; and
    5 mg of the amiloride.

11. The pharmaceutical composition of claim 1, comprising:
    10 mg of the amlodipine;
    12.5 mg of the chlorthalidone; and
    10 mg of the amiloride.

12. The pharmaceutical composition of claim 1, comprising:
    10 mg of the amlodipine;
    25 mg of the chlorthalidone; and
    5 mg of the amiloride.

13. The pharmaceutical composition of claim 1, comprising:
    10 mg of the amlodipine;
    25 mg of the chlorthalidone; and
    10 mg of the amiloride.

14. The pharmaceutical composition of claim 1, wherein the pharmaceutical composition is a fixed dose combination.

15. A method for treating resistant hypertension in a subject in need thereof, comprising:
    administering a therapeutically effective amount of the pharmaceutical composition of claim 1 to the subject.

16. The method of claim 15, wherein the resistant hypertension is low-renin/low-aldosterone resistant hypertension.

17. A method for treating a target organ damage in a subject with resistant hypertension, comprising:
    administering a therapeutically effective amount of the pharmaceutical composition of claim 1 to the subject.

18. The method of claim 17, wherein the target organ damage is left ventricular hypertrophy, benign arterioles nephrosclerosis, malignant arterioles nephrosclerosis, renal failure, retinal arteriosclerosis, hypertensive fundus disease, cerebral ischemia, cerebral hemorrhage, acute myocardial infarction or transient cerebral insufficiency.

* * * * *